(12) United States Patent
Bernhardt et al.

(10) Patent No.: US 10,517,746 B2
(45) Date of Patent: Dec. 31, 2019

(54) AIR CONTROL SYSTEM FOR ENHANCING A CONNECTION BETWEEN A LIMB LINER AND A LIMB PROSTHESIS

(71) Applicant: Comfort Products, Inc., Croydon, PA (US)

(72) Inventors: Frederick S. Bernhardt, Croydon, PA (US); Peter V. Panuncialman, Melrose Park, IL (US)

(73) Assignee: Comfort Products, Inc., Croydon, PA (US)

( * ) Notice: Subject to any disclaimer, the term of this patent is extended or adjusted under 35 U.S.C. 154(b) by 0 days.

(21) Appl. No.: 15/464,285

(22) Filed: Mar. 20, 2017

(65) Prior Publication Data

US 2017/0266021 A1    Sep. 21, 2017

Related U.S. Application Data

(60) Provisional application No. 62/311,377, filed on Mar. 21, 2016.

(51) Int. Cl.
| | | |
|---|---|---|
| *A61F 2/78* | (2006.01) | |
| *A61F 2/76* | (2006.01) | |
| *A61F 2/80* | (2006.01) | |
| *A61F 2/66* | (2006.01) | |

(Continued)

(52) U.S. Cl.
CPC .............. *A61F 2/7843* (2013.01); *A61F 2/66* (2013.01); *A61F 2/76* (2013.01); *A61F 2/80* (2013.01); *A61F 2002/607* (2013.01); *A61F 2002/6614* (2013.01); *A61F 2002/6854* (2013.01); *A61F 2002/805* (2013.01)

(58) Field of Classification Search
CPC .... A61F 2/7843; A61F 2/76; A61F 2002/802; A61F 2002/805; A61F 2002/807; A61F 2002/501; A61F 2002/5012
See application file for complete search history.

(56) References Cited

U.S. PATENT DOCUMENTS

| | | |
|---|---|---|
| 3,889,301 A | 6/1975 | Bonner, Sr. |
| 5,156,629 A | 10/1992 | Shane et al. |
| 5,314,497 A | 5/1994 | Fay et al. |

(Continued)

FOREIGN PATENT DOCUMENTS

EP    0019612 A1 *    5/1980    ............... A61F 1/02

OTHER PUBLICATIONS

Translation of EP0019612A1 (Year: 1980).*

*Primary Examiner* — Christie L Bahena
(74) *Attorney, Agent, or Firm* — LaMorte & Associates P.C.

(57) ABSTRACT

A system for joining a limb liner to a prosthesis. The prosthesis has a socket that is joined to the remainder of the prosthesis using a hub assembly. The hub assembly includes a first hub and a second hub. The first hub is disposed within the interior of the socket. The second hub is disposed outside the interior of the socket. An air conduit extends through the hub assembly that enables air to be drawn into the socket and/or vented from the socket. An inflatable interface is disposed within the socket. The inflatable interface receives air through the air conduit in the hub assembly. The inflatable interface is capable of filling any gaps that may exist between a limb liner being worn by an amputee and the socket.

15 Claims, 6 Drawing Sheets

(51) Int. Cl.
*A61F 2/60* (2006.01)
*A61F 2/68* (2006.01)

(56) References Cited

U.S. PATENT DOCUMENTS

| | | | |
|---|---|---|---|
| 5,387,245 A | 2/1995 | Fay et al. | |
| 5,464,443 A | 11/1995 | Wilson et al. | |
| 5,549,709 A | 8/1996 | Caspers | |
| 5,724,714 A | 3/1998 | Love | |
| 5,728,170 A * | 3/1998 | Becker | A61F 2/7843 623/33 |
| 5,735,906 A | 4/1998 | Caspers | |
| 5,746,772 A | 5/1998 | Jacobs | |
| 5,904,722 A | 5/1999 | Caspers | |
| 6,149,691 A | 11/2000 | Fay et al. | |
| 6,508,842 B1 | 1/2003 | Caspers | |
| 6,554,868 B1 | 4/2003 | Caspers | |
| 6,979,355 B1 * | 12/2005 | Slemker | A61F 2/80 623/34 |
| 7,670,386 B2 | 3/2010 | Ezenwa | |
| 9,017,420 B1 | 4/2015 | Bernhardt | |
| 2002/0087215 A1 | 7/2002 | Caspers | |
| 2002/0088384 A1 | 7/2002 | Bernhardt | |
| 2002/0091449 A1 | 7/2002 | Caspers et al. | |
| 2003/0078674 A1 | 4/2003 | Philips | |
| 2003/0181990 A1 | 9/2003 | Philips | |
| 2004/0098136 A1 | 5/2004 | Caspers | |
| 2004/0137098 A1 | 7/2004 | Karason | |
| 2004/0143345 A1 | 7/2004 | Caspers | |
| 2008/0147204 A1 | 6/2008 | Ezenwa | |
| 2008/0243266 A1 * | 10/2008 | Haynes | A61F 2/68 623/34 |
| 2010/0070051 A1 | 3/2010 | Carstens | |
| 2010/0094432 A1 * | 4/2010 | Mackenzie | A61F 2/68 623/34 |
| 2013/0123940 A1 | 5/2013 | Hurley et al. | |
| 2013/0173020 A1 | 7/2013 | Slemker et al. | |
| 2014/0039643 A1 * | 2/2014 | Tompkins | A61F 2/80 623/34 |
| 2014/0058529 A1 | 2/2014 | Schober et al. | |
| 2014/0222165 A1 * | 8/2014 | Mackenzie | A61F 2/80 623/34 |

* cited by examiner

AIR CONTROL SYSTEM FOR ENHANCING A CONNECTION BETWEEN A LIMB LINER AND A LIMB PROSTHESIS

RELATED APPLICATIONS

The present application claims the benefit of U.S. Provisional Patent Application No. 62/311,377, filed Mar. 21, 2016.

BACKGROUND OF THE INVENTION

1. Field of the Invention

In general, the present invention relates to air control systems that are used to either create a vacuum or inflate an inflatable liner at the interface between a partially amputated limb and a limb prosthesis. More, particularly, the present invention relates to the structure of such an air control system and its structure in relation to a limb prosthesis.

2. Prior Art Description

Many people who have amputated limbs or partially amputated limbs rely upon prosthetics to live more active lives. When a person is fitted for a limb prosthesis, that person may also be fitted with a limb liner. A limb liner is typically worn over the portion of the limb that remains on the body. A limb liner is an elastomeric device that is pulled over the residual limb. The liner conforms to the shape of the residual limb and creates a strong frictional attachment to the skin of the residual limb. In many instances, a metal locking pin extends from the tip of the limb liner. The locking pin is used to engage the prosthetic limb when a prosthetic limb is mated with the limb liner. As such, the limb liner acts as the anchor for retaining the limb prosthesis onto the residual limb.

To manufacture a limb prosthesis, a cast is first taken of the limb liner while the limb liner is being worn. The cast is used to produce a socket. The socket is then attached to the limb prosthesis. The socket of the limb prosthesis is the portion of the prosthesis that mates with the limb liner and conforms to the shape of the limb liner and the underlying residual limb. In this manner, the limb prosthesis will properly fit onto the limb liner and residual limb.

Amputees commonly retain their prosthetic limbs for many years. During this time, the amputee may gain weight, lose weight, lose muscle mass, or otherwise undergo physiological changes. Furthermore, amputees may retain water, have limb swelling or undergo other physical changes that can cause the size of the amputated residual limb to vary. As the residual limb changes in size and/or contour, the configuration of the limb liner also changes. As a result, the shape of the limb liner may no longer match the shape of the socket in the prosthetic limb. This mismatch in shape can create gaps between the limb liner and the socket of the prosthesis. The gaps can cause the prosthesis to feel loose in certain places and overly tight in others. Furthermore, the gaps can cause physical discomfort by causing chafing against the residual limb.

In the prior art, fabric-based liner socks have been worn to fill gaps between the limb liner and the limb prosthesis. Prior art liner socks are basically knitted or woven socks that are worn over the limb liner. The liner sock becomes compressed at points of contact between the limb liner and the limb prosthesis. The liner sock is less compressed in areas of gaps. Accordingly, the liner sock helps to fill the gaps between the limb liner and the prosthesis.

The ability of a knitted or woven sock to fill a gap is limited to gaps that are typically less than $\frac{1}{32}^{nd}$ of an inch wide. In situations where larger gaps exist, amputees typically turn to a gel liner or multiple layers of knitted socks. Gel liners are socks molded from an elastomeric material. These gel liners are worn around the limb liner when the limb liner is inserted into the socket of the prosthesis. The problem associated with such gel liners is one of compromise. The socket of the prosthesis is created from a mold of the limb liner. Accordingly, these two elements tend to be very close in shape. If the amputee's residual limb undergoes some physiological change, then that change may be localized. That is, only certain segments of the amputee's residual limb change, while the majority remains relatively the same. When a gel liner or multiple socks are used, the padding adds thickness to the entire limb liner. Accordingly, the segments of the limb liner that fit properly are now tight. In many situations, the discomfort created by a gel liner outweighs its benefits. Accordingly, gel liners are made thin, but not too thin that they cannot fill a gap. This compromise often makes gel liners either too loose or too tight in some separate areas.

The disadvantages of a gel liner can be avoided by the use of an air controlled interface, such as a vacuum connection or the use of an inflatable liner. In the prior art, several inflatable liners have been invented for use between amputated limbs and prostheses. The inflatable liners can be selectively inflated to provide an adjustable interface between the residual limb and the prosthesis. In both U.S. Patent Application Publication No. 2003/0078674, to Phillips, entitled Socket Insert Having A Bladder System, and U.S. Patent Application Publication No. 2003/0181990, to Phillips, entitled Socket Insert Having A Bladder System, an inflatable bladder system is shown where the inflatable bladder is formed as part of the prosthetic's socket. These references provide bladders in only some parts of the socket. Accordingly, there is no guarantee that the bladders will fill any gaps that may exist between the amputee's limb and the socket of the prosthetic.

In U.S. Pat. No. 5,156,629 to Shane, entitled Pneumatic Prosthetic Insert, and U.S. Pat. No. 5,387,245 to Fay, entitled Inflatable Prosthetic Liners, inflatable limb liners are disclosed. These inflatable limb liners are designed to take the place of the elastomeric limb liner around which the socket of the prosthesis is molded. By eliminating the elastomeric limb liner, room is made for the inflatable limb liner.

As will be understood among amputees, residual limbs vary widely in shape and contour from patient to patient. This is why the socket of a prosthesis is custom molded to a limb liner. By replacing the limb liner with a single-sized inflatable liner, it would be impossible to create a quality interconnection between the residual limb and prosthetic socket of most amputees. Furthermore, inflatable limb liners lack the physical structure to support a connector pin. The connector pin creates the strongest mechanical interconnection between the limb liner and the prosthetic limb. Without a connector pin, many amputees would not be able to keep the prosthetic limb attached to their bodies during normal everyday activities.

A need therefore exists for a new type of air controlled interface that is designed to remove or add air between a prosthetic limb socket and a limb liner having a connector pin, where the air controlled interface has no adverse effect upon the ability of the limb liner pin to interconnect with the limb prosthesis. This need is met by the present invention as described and claimed below.

SUMMARY OF THE INVENTION

The present invention is a prosthesis and a system for joining a limb liner, worn by an amputee, to the prosthesis.

The prosthesis has a socket that is sized to receive a limb liner being worn by an amputee. The socket has an open top, a bottom, and an interior that is accessible through the open top. The socket is joined to the remainder of the prosthesis using a hub assembly. The hub assembly includes a first hub and a second hub that are joined together and a segment of said bottom of said socket is interposed between said first hub and said second hub within said hub assembly. The first hub is disposed within the interior of the socket, and is preferably separate and distinct from the socket. The first hub rests within a relief that is formed in the bottom of the socket.

A second hub is disposed outside the interior of the socket. The second hub is also preferably separate and distinct from the socket. The first hub and the second hub are joined together with mechanical fasteners through the bottom of the socket to form the hub assembly.

An air conduit extends through the hub assembly that enables air to be drawn into the socket and/or vented from the socket. An inflatable interface is disposed within the socket. The inflatable interface receives air through the air conduit in the hub assembly. The inflatable interface is capable of filling any gaps that may exist between a limb liner being worn by an amputee and the socket. Said air conduit is se arate distinct and offset from a pin receptacle.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention interface can be embodied for use with an arm prosthesis or a transfemoral leg prosthesis, the embodiment illustrated shows the interface being used on a transtibial leg prosthesis. This embodiment is selected in order to set forth the best mode contemplated for the invention. The illustrated embodiment, however, is merely exemplary and should not be considered a limitation when interpreting the scope of the claims.

Figure 1:
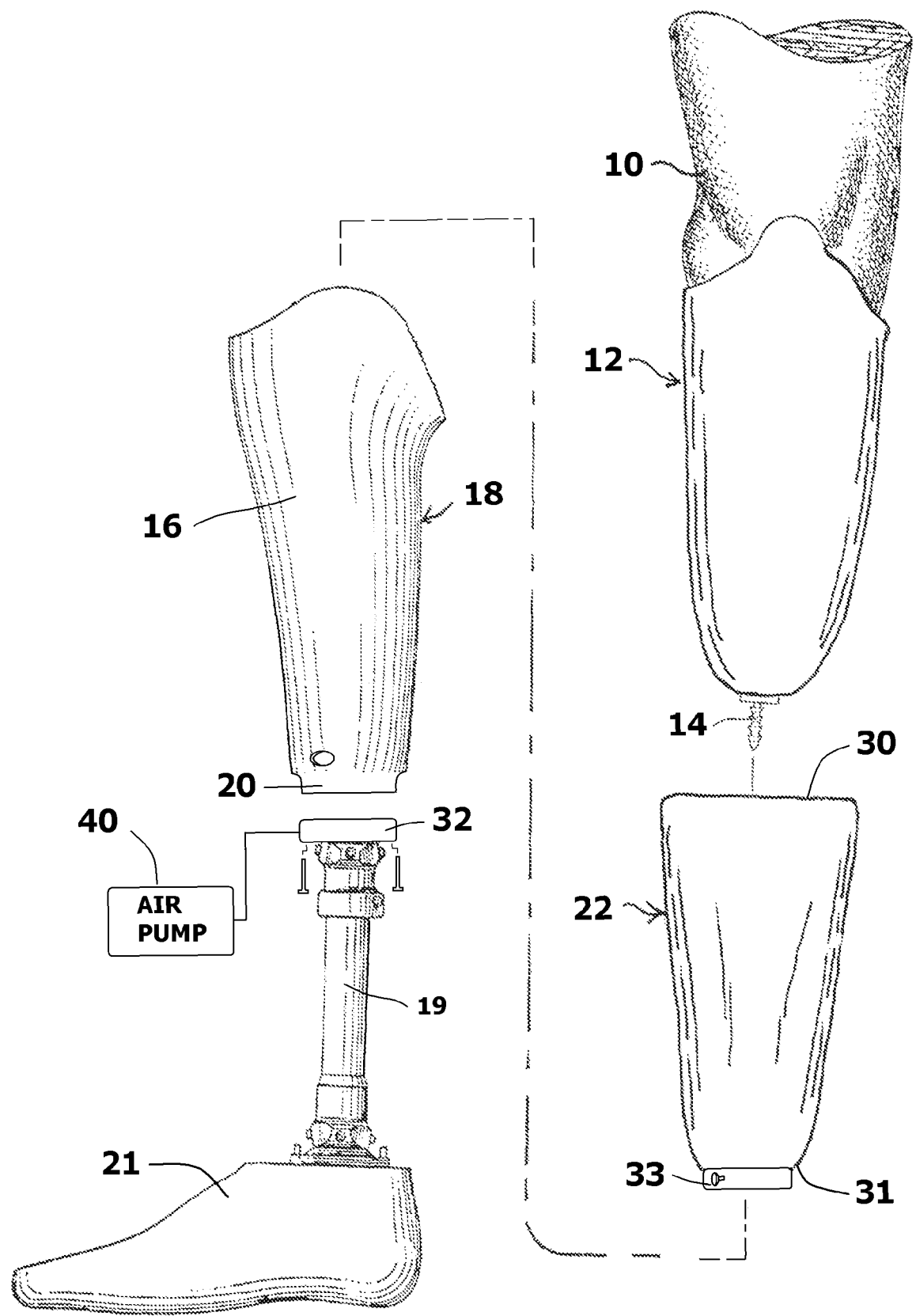
FIG. 1 is an exploded view of an amputee's prosthesis and mounting system that includes a limb liner, a prosthesis, and an inflatable interface.
Figure 2:
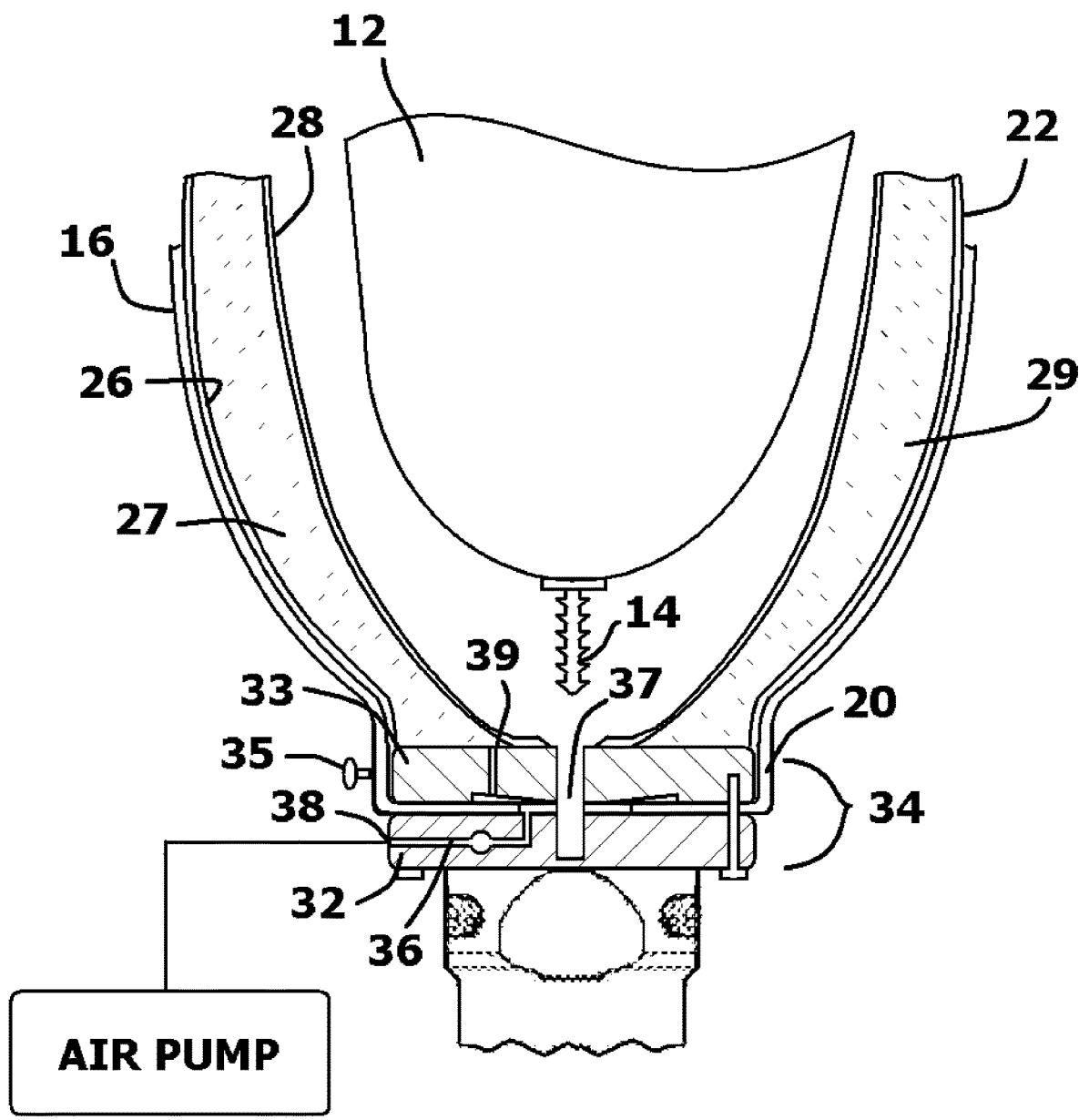
FIG. 2 is a selectively cross-sectioned view of the embodiment of FIG. 1 shown in an assembled condition.

Referring to FIG. 1 and FIG. 2, a residual limb 10 of an amputee is shown. The residual limb 10 is fitted with an elastomeric limb liner 12 using traditional fitting techniques. The limb liner 12 covers the residual limb 10. A connector pin 14 extends from the bottom of the limb liner 12. The connector pin 14 is used to interconnect the limb liner 12 with the socket 16 of a limb prosthesis 18.

The limb prosthesis 18 can have many shapes, depending upon the manufacturer's model and the needs of the amputee. The limb prosthesis 18 includes a socket 16 for receiving the amputee's residual limb 10 surrounded by the limb liner 12. Typically, the socket 16 is fabricated by taking a mold of the amputee's residual limb 10 while wearing a limb liner 12. Accordingly, the socket 16 has an internal shape that is nearly identical to the external shape of the limb liner 12, while worn on the residual limb 10. The main difference is a disc-shaped hub relief 20 that is formed at the bottom of the limb liner 12.

An inflatable interface 22 is provided. The purpose of the inflatable interface 22 is to compensate for any gaps that may form between the socket 16 of the prosthesis 18 and the limb liner 12. In this manner, the limb liner 12 always feels secure within the socket 16 when worn. The inflatable interface 22 has an exterior layer 26 and an interior layer 28. An inflatable gap 27 exists between the exterior layer 26 and the interior layer 28. The inflatable gap 27 can selectively expand and contract depending upon the air pressure within the gap 27. The inflatable gap 27 may be empty. However, in the preferred embodiment, a layer of open cell foam 29 may be interposed between the exterior layer 26 and the interior layer 28. In this manner, the inflatable gap 27 will expand to the shape of the open cell foam 29 when vented to ambient air pressure. This provides the inflatable gap 27 with the ability to self-inflate by venting the inflatable gap 27 to atmosphere.

The inflatable interface 22 has an open top 30 and a closed bottom 31. The open top 30 receives the limb liner 12. The opposite closed bottom 31 of the inflatable interface 22 is closed, with the exception of a small opening for the passage of the connector pin 14.

An upper inflation hub 33 is affixed to the inflatable interface 22 at the closed bottom 31 of the inflatable interface 22. The upper inflation hub 33 is sized to fit within the disc shaped hub relief 20 that is molded into the bottom of the limb liner 12. In this manner, the presence of the upper inflation hub 33 does not interfere with the fit of the limb liner 12 within the socket 16.

The limb prosthesis 18 illustrated is a leg prosthesis, wherein a shaft 19 extends from a prosthetic foot 21. The shaft 19 supports the socket 16. A lower inflation hub 32 is rigidly mounted to the support shaft 19 of the limb prosthesis 18 under the socket 16. The lower inflation hub 32 is rigidly mounted directly to the upper inflation hub 33, wherein an airtight seal is created between the upper inflation hub 33 and the lower inflation hub 32, with the segments of both the socket 16 and the inflatable interface 22 interposed therebetween. A central hole 37 is formed in both the upper inflation hub 33 and the lower inflation hub 32 to receive the locking pin 14 of the limb liner 12.

The upper inflation hub 33 and the lower inflation hub 32 are mechanically joined together with screws or bolts to form a hub assembly 34. The hub assembly 34 includes the locking mechanism 35 for engaging and releasing the connector pin 14 within the central hole 37. The hub assembly 34 also defines an internal air conduit 36 that extends between an air intake port 38 and an air outlet port 39. The air intake port 38 is in the upper inflation hub 33, the air outlet port 39 is in the lower inflation hub 32. The internal air conduit 36 passes through the hub assembly 34 and leads into the inflatable gap 27 within the inflatable interface 22.

An external air pump 40 is attached to the air intake port 38 that leads into the internal air conduit 36. The external air pump 40, when activated, can introduce air into the hub assembly 34. Any air introduced into the hub assembly 34 passes into the internal air conduit 36 of the hub assembly 34 and reaches the inflatable gap 27 within the inflatable interface 22. As such, the inflatable interface 22 inflates as the external air pump 40 pumps air into the hub assembly 34.

If an amputee feels as though the socket 16 of the prosthesis 18 is too loose, the amputee need only pump more air into the hub assembly 34. The inflatable interface 22 will expand and fill any existing gap spaces, thereby making the inflatable interface 22 thicker and cause the fit of the limb liner 12 to become tighter.

Figure 3:
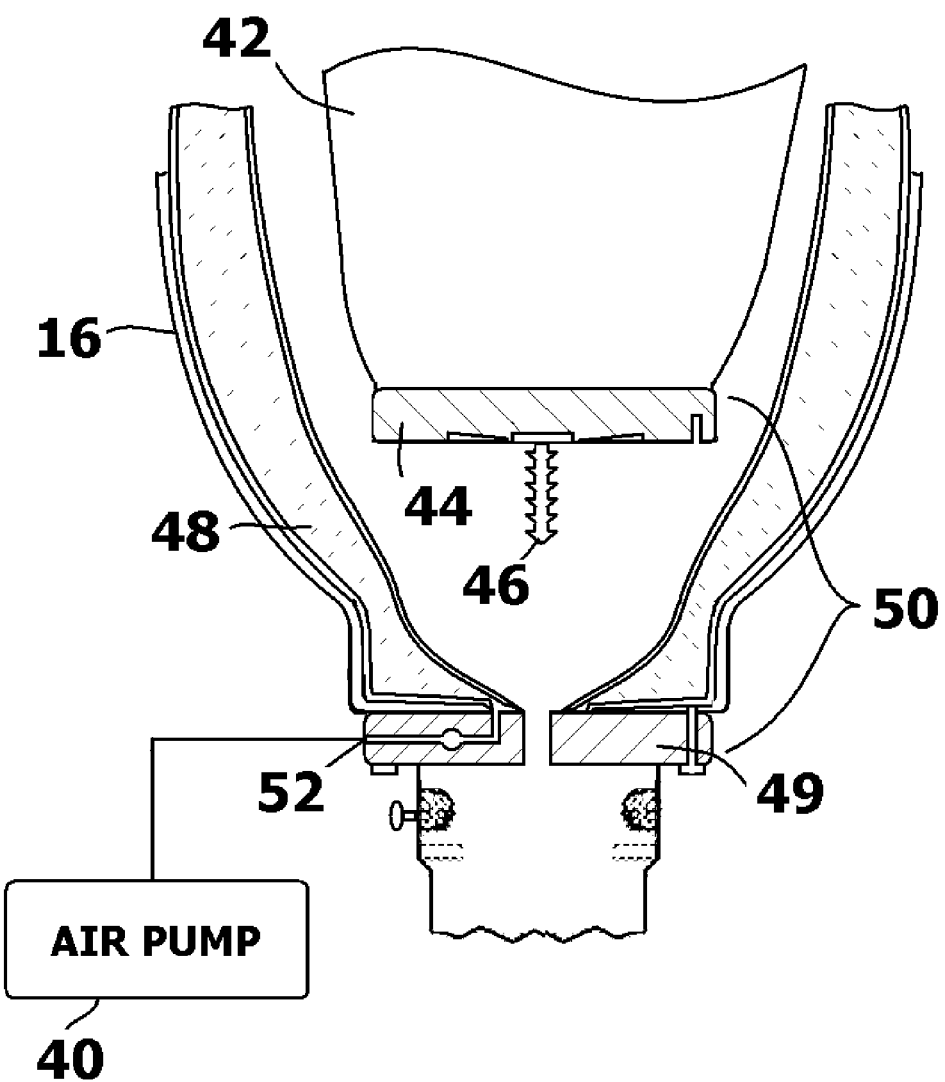
FIG. 3 is a selectively cross-sectioned view of an alternate embodiment of a mounting system, wherein the inflatable interface is a separate and distinct element.

In the embodiment of FIG. 1 and FIG. 2, the upper inflation hub 33 is connected to the inflatable interface 22. This need not be the case. An alternate configuration is shown in FIG. 3. Referring to FIG. 3, modified limb liner 42 is shown. An upper inflation hub 44 is built into the structure of the limb liner 42. The limb liner 42 has a locking pin 46. The locking pin 46 either passes through the upper inflation hub 44 or extends from the upper inflation hub 44.

An inflatable interface 48 is provided that can be selectively inflated and deflated. The inflatable interface 48 is not attached to the upper inflation hub 44. The inflatable interface 48 can be attached to the interior of the socket 16 or it can be a standalone component.

A lower inflation hub 49 is provided. The lower inflation hub 49 bolts to the upper inflation hub 44 to form a complete hub assembly 50. Once interconnected, a portion of the inflatable interface 48 is locked between the upper inflation hub 44 and the lower inflation hub 49.

An air intake port 52 is provided that is attached to an external air pump 40. The external air pump 40, when activated, can introduce air into the inflatable interface 48. Any air introduced passes into the air intake port 52 and expands the inflatable interface 48. If an amputee feels as though the socket 16 of the prosthesis 18 is too loose, the amputee need only pump in more air. The inflatable interface 48 will expand and fill any existing gap spaces, thereby making the inflatable interface 48 thicker and the fit of the limb liner 42 tighter.

Figure 4:
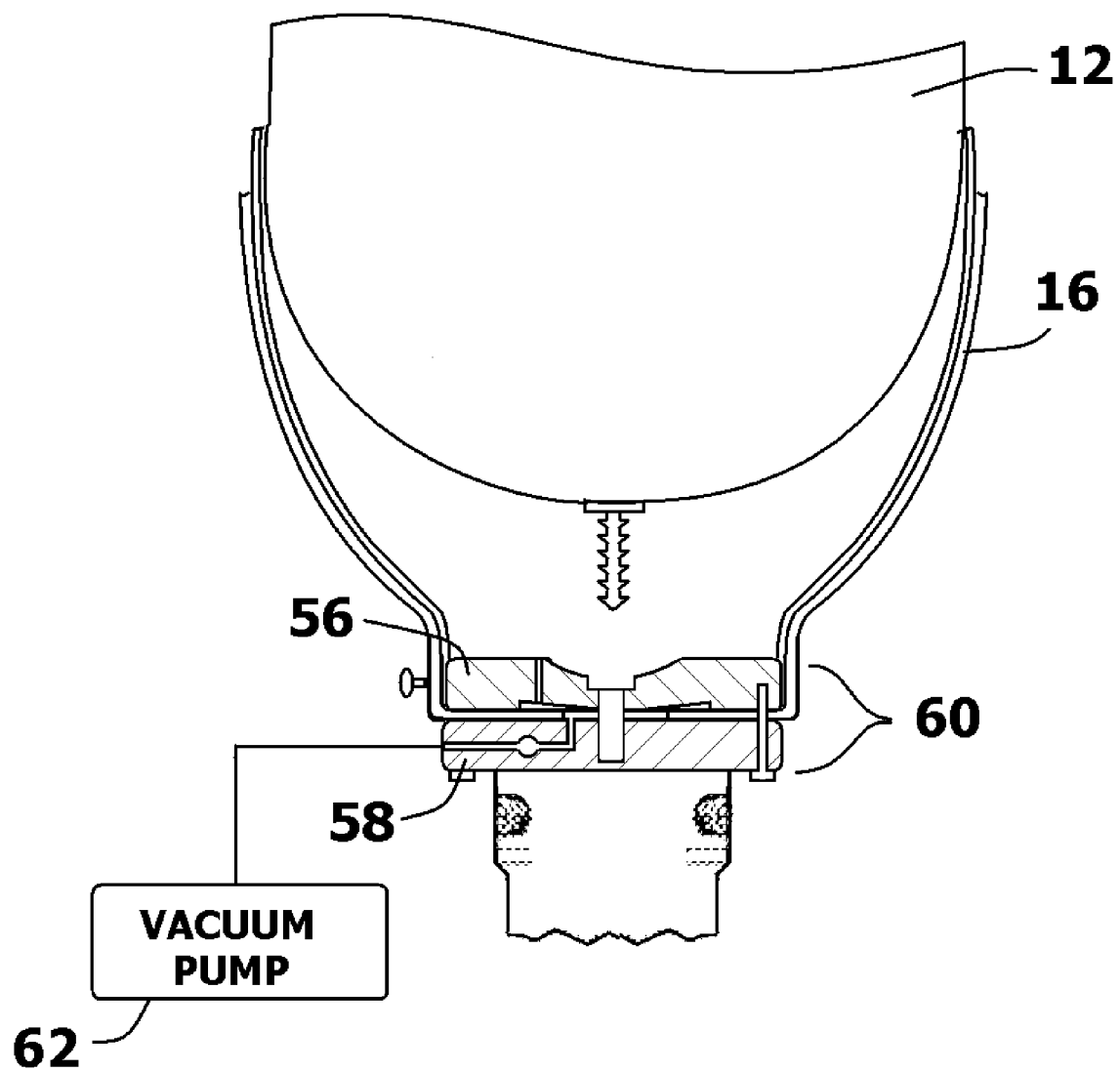
FIG. 4 is a selectively cross-sectioned view of an alternate embodiment of a mounting system, wherein a vacuum pump is utilized.

Referring to FIG. 4, another embodiment of the present invention is shown. In this embodiment no inflatable interface is used. Rather, the upper inflation hub 56 and the lower inflation hub 58 are joined directly to the socket 16, therein forming a complete hub assembly 60. The hub assembly 60 is coupled to a vacuum pump 62, rather than the air pump of previous embodiments. In this manner, the vacuum pump 62 can draw air from within the socket 16. This creates a low pressure area between the socket 16 and a limb liner 12 that helps hold the limb liner 12 in place.

Figure 5:
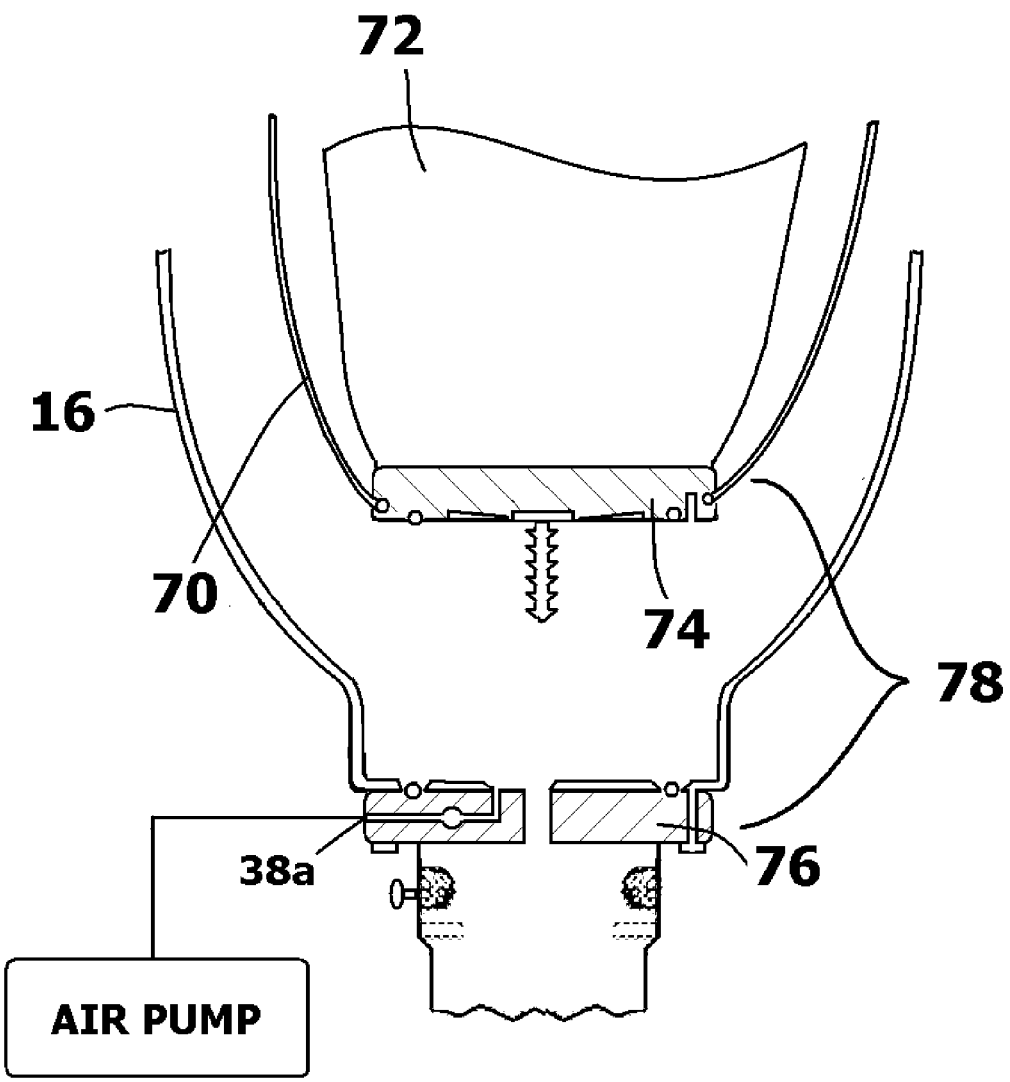
FIG. 5 is a selectively cross-sectioned view of an alternate embodiment of a mounting system, wherein the inflatable interface is incorporated as part of the limb liner.

Referring to FIG. 5, another embodiment of the present invention is shown. In this embodiment, an inflatable interface 70 is provided that is integrated into the structure of a limb liner 72. An upper inflation hub 74 is connected to the limb liner 72 and the inflatable interface 70. A lower inflation hub 76 is mounted to the socket 16. The upper inflation hub 74 and the lower inflation hub 76 mount together to form a complete hub assembly 78. When the upper inflation hub 74 and the lower inflation hub 76 are joined directly together, they form a complete internal air conduit 80 that leads from an air intake port 82 to the interior of the inflatable interface 70. The air intake port 82 is supplied with air from an air pump 40.

If an amputee feels as though the socket 16 is too loose, the amputee need only pump more air into the inflatable interface 70. The inflatable interface 70 will expand and fill any existing gap spaces, thereby making the inflatable interface 70 thicker and the fit of the limb liner 72 tighter.

Figure 6:
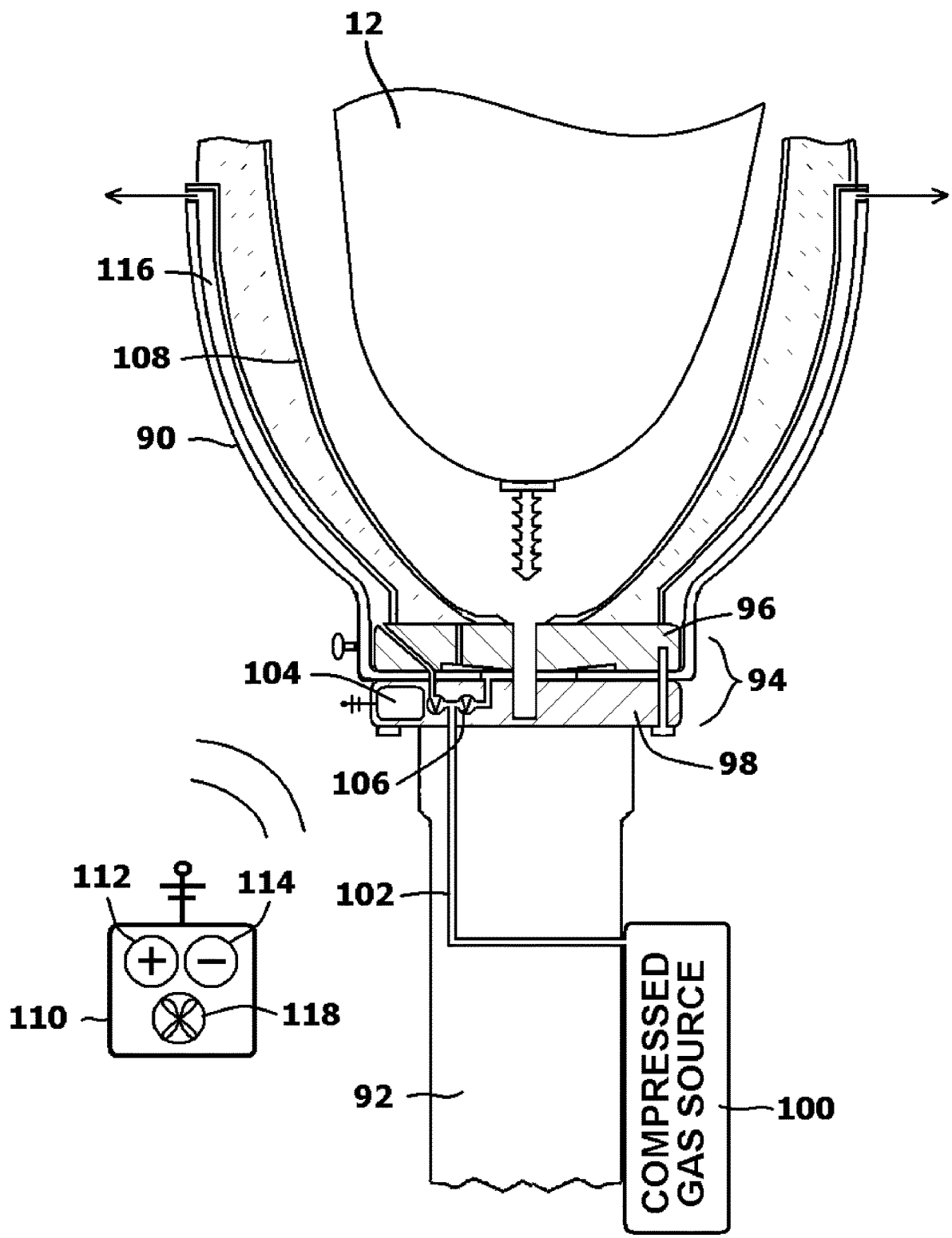
FIG. 6 is a selectively cross-sectioned view of an alternate embodiment of a mounting system, wherein a compressed air source and remote control are utilized.

Referring to FIG. 6, an embodiment is presented where a socket 90 is supported on a shaft 92 using a hub assembly 94. The hub assembly 94 has an upper inflation hub 96 and a lower inflation hub 98 that interconnect in the same manner as the previously described for the embodiment presented in FIG. 1. In this embodiment, a compressed gas source 100 is provided. The compressed gas source 100 can be a battery operated air compressor, a mechanically operated air compressor that is powered by the movement of the prosthesis, or a compressed gas cartridge, such as a 12-gram $CO_2$ cartridge. Regardless, the compressed gas source 100 is capable of providing a flowing supply of gas.

The gas generated by the compressed gas source 100 is channeled through internal conduits 102 to a valve control unit 104. The valve control unit 104 contains a first valve 106 that controls the flow of gas into and out of an inflatable interface 108. The valve control unit 104 may be manually controlled using valve control buttons. However, in the shown embodiment, the valve control unit 104 is controlled by a remote control 110. The remote control 110 has a pressure increase control 112 and a pressure decrease control 114. By pressing the controls 112, 114, a user can selectively inflate or deflate the inflatable interface 108.

In the shown embodiment, the valve control unit 104 is also connected to a vent space 116. The vent space 116 is positioned within the socket 90 surrounding the inflatable interface 108. When the valve control unit 104 directs gas flow into the vent space 116, the flow of gas acts to cool the socket 90. This cools the limb liner 12 and the residual limb in the limb liner 12. This cooling cycle can also be initiated using a vent control 118 on the remote control 110.

It will be understood that the embodiments of the present invention that are illustrated and described are merely exemplary and that a person skilled in the art can make many variations to those embodiments. For instance, the shape of the interface can vary widely to accommodate many different types of amputee limbs. Furthermore, many vent controls and miniature manual air pumps exist in the prior art. Many of those designs can be adapted for use by the present invention in place of the air pump or vacuum pump. All such embodiments are intended to be included within the scope of the present invention as defined by the claims.

What is claimed is:

1. A system for joining a limb liner, worn by an amputee, to a socket of a prosthesis, said system comprising:
   a prosthesis having a socket sized to receive a limb liner worn by an amputee, wherein said socket has an open top, a bottom, and an interior that is accessible through said open top;
   a first hub, separate and distinct from said socket, that is disposed within said interior of said socket, wherein a first air port is formed in said first hub;
   a second hub, separate and distinct from said socket, disposed outside said interior of said socket, wherein a second air port is formed in said second hub,
   mechanical fasteners that extend through said bottom of said socket to join said first hub and said second hub into a hub assembly, wherein a segment of said bottom of said socket is interposed between said first hub and said second hub within said hub assembly;
   a pin receptacle that extends through said first hub and into said second hub; and
   an air conduit that extends through said hub assembly from said first air port in said first hub to said second air port in said second hub, wherein said air conduit is separate, distinct and offset from said pin receptacle.

2. The system according to claim 1, further including an inflatable interface within said interior of said socket, wherein said inflatable interface is selectively inflated by air flowing out of said first air port through said air conduit.

3. The system according to claim 2, further including an air pump that supplies air to said inflatable interface through said second air port of said air conduit.

4. The system according to claim 2, wherein said inflatable interface is mounted to said first hub.

5. The system according to claim 1, further including a vacuum pump that draws air through said air conduit.

6. The system according to claim 1, wherein a relief is formed in said bottom of said socket and said first hub seats within said relief.

7. A system for joining a prosthesis to a residual limb of an amputee, said system comprising:
   a limb liner to be worn over the residual limb, wherein said limb liner has a locking pin extending therefrom;
   a prosthesis having a socket sized to receive said limb liner, wherein said socket has an open top, a bottom opposite said open top, and an interior that extends from said open top to said bottom;
   a first hub disposed within said interior of said socket;
   a second hub disposed outside said interior of said socket, wherein said second hub mechanically connects with said first hub to form a hub assembly, wherein said hub assembly defines an air conduit that leads through said second hub and said first hub, therein enabling air to flow into said interior of said socket from outside said socket;
   a receptacle for receiving said locking pin that is separate, distinct and offset from said air conduit, wherein said receptacle extends through said first hub and into said second hub, and
   an inflatable interface disposed between said socket and said limb liner, wherein said inflatable interface is selectively inflated through said air conduit.

8. The system according to claim 7, further including an air pump that supplies air to said inflatable interface through said air conduit.

9. The system according to claim 8, wherein said inflatable interface is mounted to said hub assembly.

10. The system according to claim 7, wherein a relief is formed in said bottom of said socket and said first hub is seated within said relief.

11. A prosthesis to be worn on a limb with a limb liner, said prosthesis comprising:
    a prosthetic foot;
    a shaft extending from said prosthetic foot, wherein said shaft terminates away from said prosthetic foot at a second hub;
    a socket having an open top, a bottom, and an interior that is accessible through said open top; and
    a first hub disposed within said interior of said socket;
    wherein said first hub and said second hub are joined together with mechanical fasteners through said bottom of said socket to form a hub assembly;
    wherein said first hub has a first port and said second hub has a second port, wherein said hub assembly defines an air conduit that extends through said hub assembly from said first port to said second port when said first hub and said second hub are joined; and
    a pin receptacle extending through said first hub and into said second hub, wherein said pin receptacle is accessible within said interior of said socket, and wherein said receptacle is separate and distinct from said air conduit.

12. The system according to claim 11, further including an inflatable interface within said interior of said socket, wherein said inflatable interface is selectively inflated by air flowing through said air conduit.

13. The system according to claim 12, further including an air pump that supplies air to said inflatable interface through said air conduit.

14. The system according to claim 12, further including a compressed gas source coupled to said shaft that supplies gas to said inflatable.

15. The system according to claim 11, further including a vacuum pump that draws air through said air conduit.

* * * * *